United States Patent [19]

Hoffman

[11] Patent Number: 4,635,641

[45] Date of Patent: Jan. 13, 1987

[54] MULTI-ELEMENT ELECTRODE

[75] Inventor: Kent C. Hoffman, Cockeysville, Md.

[73] Assignee: Murray Electronics Associates Limited, Hunt Valley, Md.

[21] Appl. No.: 788,215

[22] Filed: Oct. 16, 1985

[51] Int. Cl.⁴ ............................................. A61B 5/04
[52] U.S. Cl. .................................... 128/639; 128/641; 128/783; 128/798; 128/802
[58] Field of Search ................ 604/20; 128/639, 640, 128/641, 802, 803, 783, 798, 82.1, 644, 799, 384

[56] References Cited

U.S. PATENT DOCUMENTS

| | | | |
|---|---|---|---|
| 2,555,037 | 5/1951 | Jensen | 128/803 |
| 3,122,137 | 10/1961 | Erlanger | 604/20 |
| 3,746,004 | 1/1973 | Jankelson | 128/803 |
| 3,848,600 | 11/1974 | Patrick, Jr. et al. | 128/783 |
| 4,062,364 | 12/1977 | Masaki | 128/803 |
| 4,082,086 | 4/1978 | Page et al. | 128/640 |
| 4,367,755 | 1/1983 | Bailey | 128/802 |
| 4,524,087 | 6/1985 | Engel | 128/640 |

Primary Examiner—Kyle L. Howell
Assistant Examiner—Randy Citrin
Attorney, Agent, or Firm—Nixon & Vanderhye

[57] ABSTRACT

A multi-element body electrode for applying an electric signal to the skin and tissue of a living subject is disclosed. The apparatus comprises at least two metal film electrode elements affixed to an adhesive coated thin clear plastic film which extends beyond the edges of the electrodes to hold the electrodes in place on the skin. Between the electrodes is an opening which permits proper placement of the electrodes relative to the injury, and permits access to the injury.

10 Claims, 11 Drawing Figures

4,635,641

MULTI-ELEMENT ELECTRODE

This invention is generally directed to a multi-element body electrode for therapeutic and diagnostic applications in medical and veterinary use. The subject invention is related to the copending and commonly assigned applications Ser. No. 711,044, filed Mar. 12, 1985, Ser. No. 783,093 filed Oct. 2, 1985 and Ser. No. 788,216 filed Oct. 16, 1985, the entire disclosures of which are hereby incorporated by reference.

BACKGROUND OF THE INVENTION

Numerous types of electrodes have been used in the medical field, for both diagnostic applications such as EKG, EMG and EEG and therapeutic applications such as electrical muscle stimulators, transcutaneous electrical nerve stimulators and iontophoresis drug delivery stimulators. The need to place electrodes at the correct locations has long been recognized as important as well as the need to use electrodes of a correct size. The requirements for correct placement and correct size become even more important for electrical signals that are monophasic or asymmetrical in shape. Two or more electrodes of the same or varying sizes are individually placed on the patient undergoing some form of electrotherapy or diagnostic procedure. In many cases, optimum results are not obtained because the electrodes are not placed on the subject in the correct fashion.

It is often necessary to establish a localized electrical contact with the external body surface of a living subject. Such contact is typically achieved by the use of electrically conductive electrodes having extended surface areas placed in electrical contact with a desired portion of an external body surface through an intermediate electrode gel, liquid or other preparation designed to ensure good and continuous electrical contact between the living body surface and the conductive electrode surface. Such electrical connections to living subjects are now commonly required for therapeutic and diagnostic applications in both medical and veterinary usage. For example, electro-therapeutic stimulation has now been recognized to promote the healing of bones and other body tissues and/or to have other advantageous physiological effects. Many diagnostic techniques (e.g., electrocardiograms) also require electrical connections to body surfaces so as to monitor electrical body surface potentials.

U.S. Pat. No. 3,848,608 discloses a cutaneous stimulator which includes a plurality of pairs of electrodes and ventilation holes located in a ground plane between each adjacent pair of electrodes. This stimulator does not provide an arrangement of electrodes relative to the holes such that therapeutic current density is particularly determined in the vicinity of the holes. Further the arrangement disclosed in this reference does not necessarily provide electrode location control or easy access to the injury being treated.

SUMMARY OF THE INVENTION

In brief summary, the exemplary embodiment of this invention provides two or more spaced-apart conductive patches with an adhesive boundary extending at least part way about the edges of the patches. The adhesive boundary may comprise a relatively larger adhesive-backed, flexible insulating sheet patch with the relatively smaller conductive patches being affixed therewithin at predetermined proper relative locations (on the one adhesive-coated side). The adhesive-coated border around at least a portion of the electrodes (and preferably completely thereabout) permits the electrodes to be adhesively affixed to treatment locations where electrodes cannot easily be affixed by traditional wrapping techniques. Such an adhesive border forms an occlusive seal with hair, fur and external body tissue surfaces at a time when the treatment site is still relatively clean and dry.

The insulating sheet has at least one aperture therein so as to provide access aperture(s) to the treatment site. To facilitate storage, transport, etc., a release liner is also preferably included and is releasably attached to and covering the otherwise exposed adhesive-backing of the insulating sheet prior to its intended usage. Such a release liner typically is formed of two parts so that the flexible electrode assembly can be slightly flexed to permit easy fingertip access to an edges of the liner thus facilitating its easy removal just prior to the time of intended usage.

Electrical snap-on connection terminals are preferably affixed to each conductive patch and extend backwards through a further aperture in the insulating sheet so as to permit ready electrical connection of a suitable electrical lead from an electrical signal generator or other conventional treatment/diagnostic apparatus. The conductive patches of the assembly are preferably flexible and may be formed from thin metal foil patches pre-laminated to their own thin insulating coating so as to provide added structural strength and to facilitate adhesion to the adhesive-backed insulating patch.

These as well as other objects and advantages of the invention will be better appreciated by carefully reading the following detailed description of the presently preferred exemplary embodiments of this invention taken in conjunction with the accompanying drawings.

DETAILED DESCRIPTION

Figure 1:
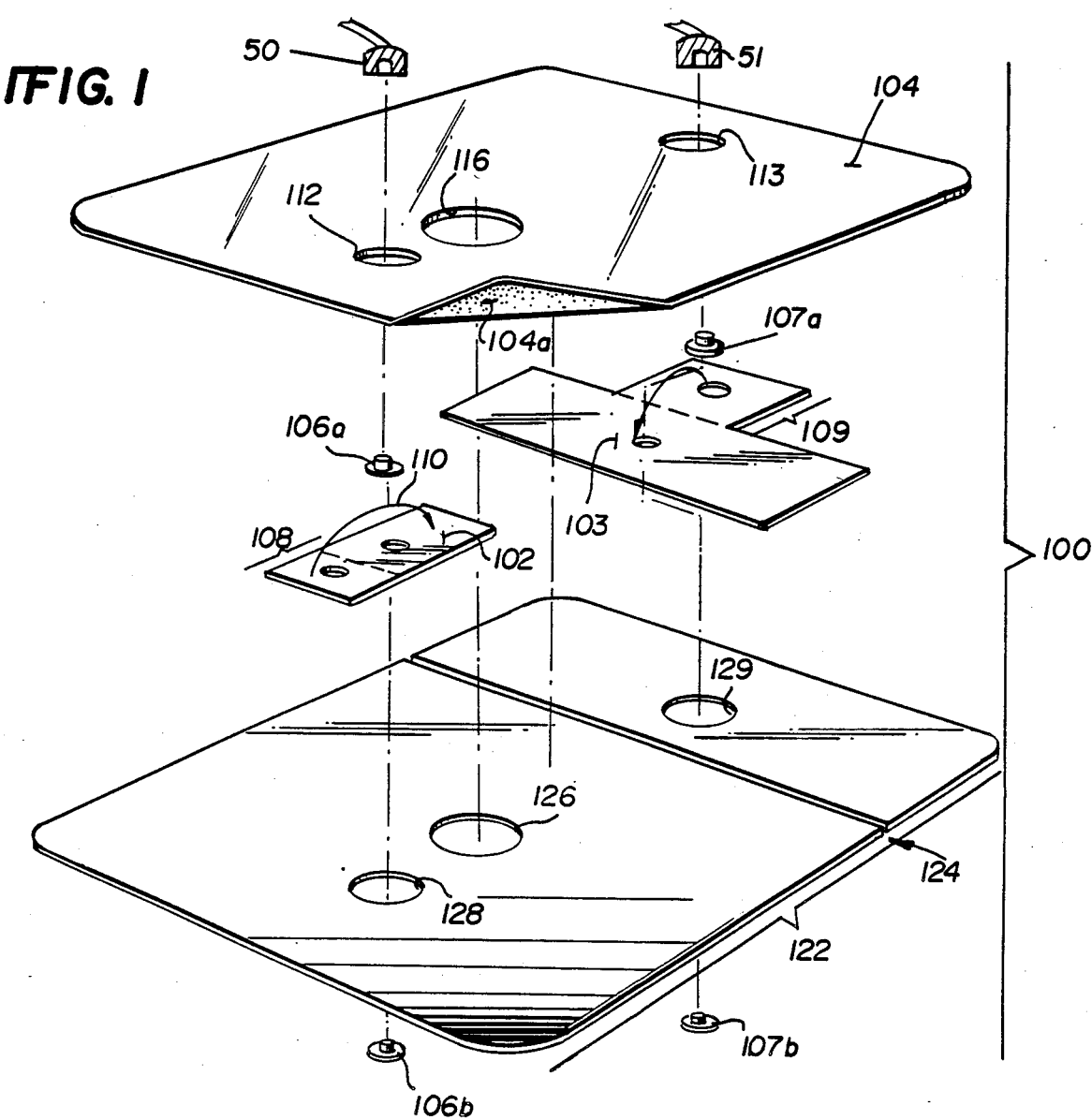
FIG. 1 is an exploded perspective view of the various components used in an exemplary embodiment of the adhesively applied multi-element electrode of this invention.

This invention relates to multiple element electrodes that have predetermined relative sizes and locations relative to an aperture in a common substrate which is applied as a single unit, with the aperture conveniently being used to (1) properly locate the electrodes vis-a-vis the desired treatment site and (2) provide access to the treatment site after affixation of the electrode structure. The electrode elements are constructed of a metal foil or film such as aluminum or a conductive film such as silver paint or carbon compound paint. These elements are affixed to an adhesive coated, thin, clear film such as pvc or mylar or are screened on a thin, clear film with adhesive selectively screened on at the same time. The multi-element electrode is produced with an opening or treatment site window to identify correct placement of the multi-electrode unit over the wound or injury. A release liner is provided on the back of the electrode. A two element example of this multi-element electrode that is useful for treating small skin wounds or burns is shown in FIG. 1. A monophasic or asymmetrical wave may be conventionally applied across the two elements correctly by use of different size electrical connectors or snaps that mate with the corresponding wires from a stimulator.

An important feature of this invention is that one element, identified as the treatment electrode, is maintained at a fixed and optimum distance from the other remote electrode element(s) and at the same time is maintained at a close, but fixed optimum distance from the injury by means of properly locating the treatment site window over the treatment site. Also typically important in such situations is the fact that the surface area of the treatment electrode may be smaller than the surface area of the remote electrode(s) and that a fixed size ratio and relative location is maintained between electrode elements by use of this multi-element electrode. The current density at the injury or treatment site is maintained at a correct higher therapeutic level while the current density under the remote electrode(s) is lower due to the larger surface area of the remote electrode(s). As those in the art will appreciate, when a given current level I passes through a tissue/skin electrode of a given size or area A, the resulting current density (e.g., amperes per square centimeter) is a function of I/A. Thus, for a given current level, the current density can be increased by making the electrode of smaller size or, vice versa, it can be decreased by making the electrode of larger size. And, as will also be appreciated, the distance of a given tissue mass from an electrode (and its relative location with respect to the anode-cathode current path) will also affect the actual current density through the tissue mass (e.g., a wound). In this fashion, the relative sizes and placements of anode and cathode electrodes can be used to determine the effective current density through a wound.

Typically, for repair of bone fractures, an electrode 103 of relatively large area as shown in FIG. 1, is utilized as an anode while a relatively smaller electrode 102 is applied relatively closer to a desired treatment site marker hole 116 (so as to provide an increased physiologically significant electrical current density thereabout) as a cathode electrode, and connected to the signal source (not shown) by lead wire 50. Electrical signals are then conventionally applied to the electrodes so as to achieve desired treatment effects.

It should be noted that in some medical applications the smaller electrode 102 is the anode, and thus the electrode 103 is the cathode. Furthermore, some signal sources e.g. transcutaneous nerve stimulators (TENS), supply biphasic signals to the electrodes, i.e. alternating current or waveforms with both positive and negative components. The present invention can be used with a biphasic signal having the smaller electrode 102 relatively close to the treatment site and the larger electrode 103 at a more remote location. This arrangement insures a higher density at the treatment site and a lower, non-biologically stimulative, signal at the larger electrode 103.

Figure 2:
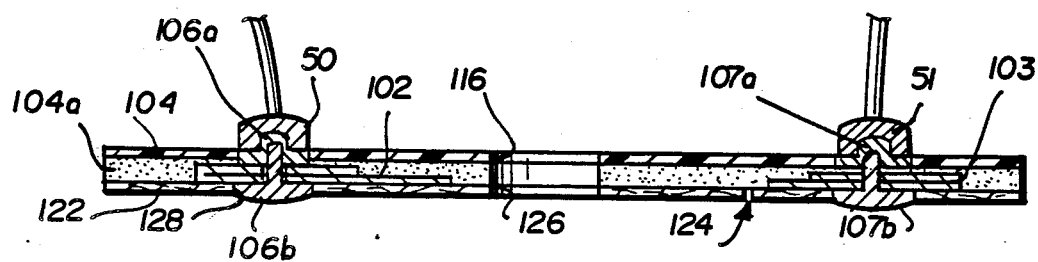
FIG. 2 is a cross-sectional view of the assembled electrode of FIG. 1.

Multi-element electrode 100 is shown in detail at FIGS. 1 and 2. Conductive metal foils 102 and 103 constitute the active electrode surfaces. In the exemplary embodiment, foils 102 and 103 are each actually a very thin (e.g., 0.00035 inch) layer of aluminum foil pre-laminated to a very thin (e.g., 0.00092) layer of polyester film (laminated to the top of structure 102 as seen in FIG. 1) so as to provide added structural strength and to facilitate adhesive affixation to a larger flexible insulating sheet 104 having a treatment site location aperture 116 located centrally (but asymetrically of the electrodes so as to be directly over the intended treatment site located nearer the smaller therapeutic electrode) and having an adhesive coating 104a on its lower side (as seen in FIG. 1). The laminated aluminum foil/polyester films 102 and 103 may be cut from commerically available material (e.g. part No. 1035 from Lam-A-Shield Incorporated, Cleveland, Ohio). The presently preferred adhesive-backed patch 104 is also cut from commerically available material (e.g. part No. 7350 from 3M Corporation which comprises a thin (e.g., 0.002 inch) insulating sheet of polypropylene with a thin (e.g., 0.0008 inch) coating of acrylic adhesive 104 on one side).

A conventional snap-on type electrical connector comprising mated parts 106a and 106b is attached to a folded-over tab portion 108 of the laminated aluminum foil structure 102. Similar parts 107a and 107b are attached to the fold-over tab portion 109 of foil 103. Since it is folded over (as indicated by arrow 110), a conductive aluminum foil surface is exposed on both the top and bottom of the thus double thickness tab portions 108 and 109 for increased structural support and electrical area connection with the snap-on devices 106a and 106b and 107a and 107b. The snap-on connector parts have a connector projection which extends backwardly (i.e. upwardly in FIG. 1) through apertures 112 and 113 respectively in the insulating patch 104 so as to be readily available for snap-on electrical connection to lead wires 50 and 51.

The flexible electrode assembly of FIGS. 1–2 also includes a releasable liner layer 122 which is normally in place covering the otherwise exposed portions of the adhesive surface 104a until the intended time of usage. Typically, the release liner 122 will include a break 124 so that the entire assembly may be slightly bent at the break to gain finger access to a free edge of the releasable liner 122 and thus facilitate its strippage from the adhesive layer 104a and ready the assembly for adhesive affixation to the desired body surface area.

Release liner 122 is shown as including apertures 126, 128 and 129. Apertures 128 and 129 typically occurs because the liner 122 already may be in place when aperture 116 is cut during manufacturing processes and apertures 128 and 129 permit the assembly of snap-on connectors while the release liner 122 remains in place thus protecting the adhesive layer 104a during manufacturing processes. However it will be appreciated that such apertures are not required since the release liner 122 is typically removed before the remainder of the electrode assembly shown in FIGS. 1–2 is adhesively affixed to a desired body surface site and used.

Figure 3:
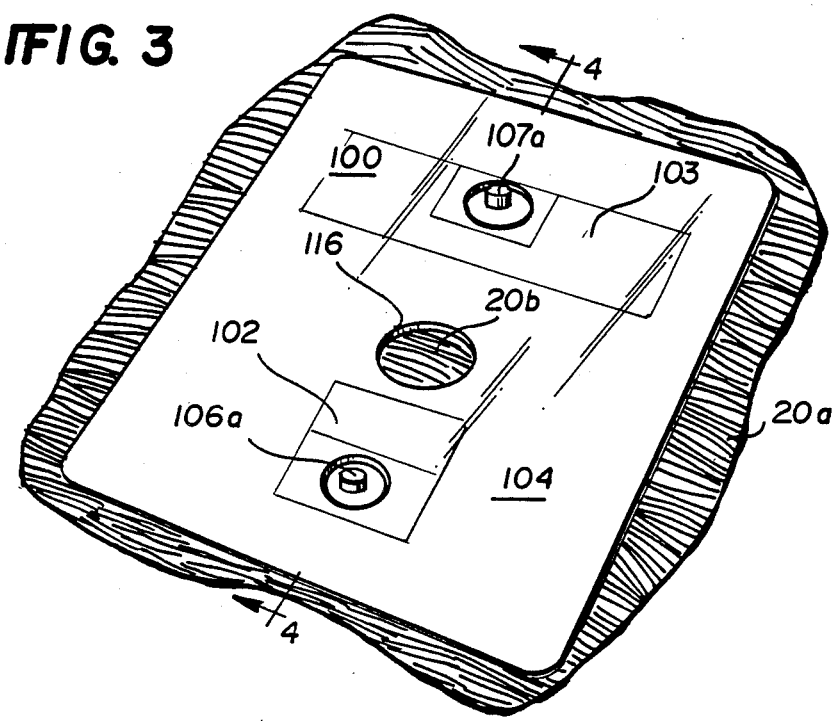
FIGS. 3 and 4 are perspective and cross-sectional views of the FIGS. 1 and 2 embodiment in place with the external body surface of a living subject.
Figure 4:
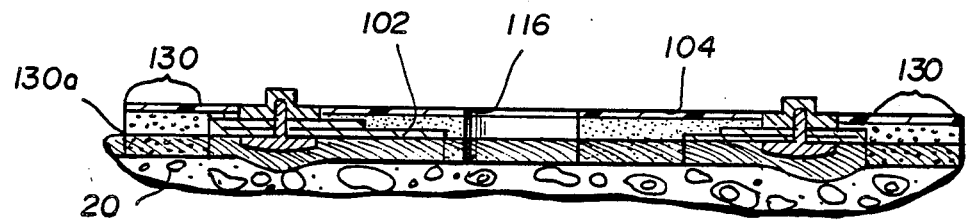

FIG. 3 depicts the electrodes of FIGS. 1–2 with the releasable liner 122 removed and the remainder of the assembly adhesively secured in place to a desired external body surface 20a of a living subject. Typically, the treatment site 20a should be clean and the connector end of cables 50 and 51 may be snapped onto the snap connectors 106a and 107a to installation of the electrode patches onto the treatment site. Once the protective releasable liner 122 has been removed so as to expose a boundary 130 of adhesive 104a, the assembly is positioned with the treatment aperture 116 over the injury site 20b and pressed firmly thereto so as to assure a good adhesive bond. As shown in the cross-sectional view of FIG. 4, the boundary areas 130 will include an adhesively sealed and occluded area 130a which incorporates any contiguous body hair (or fur) so as to provide a substantially impervious seal between the external surface of living body 20 and the periphery of the conductive electrodes 102 and 103.

Figure 5:
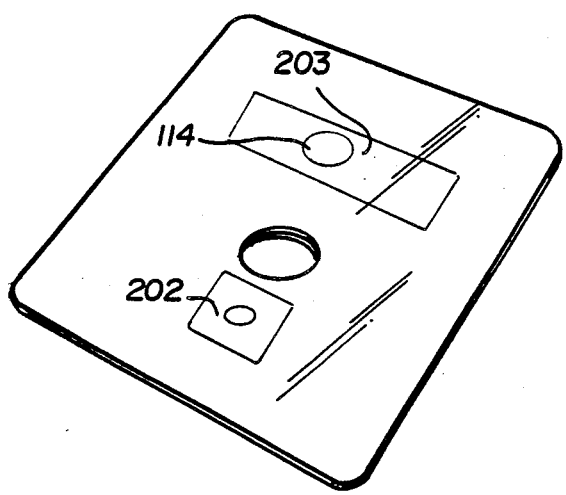
FIGS. 5-9 are perspective views of other exemplary embodiments of the invention.

As shown in FIG. 5 (having electrodes 202, 203), an electrode patch e.g. 203 can have an aperture 114 extending therethrough for receiving an electrode gel preparation material in the space located between the electrode patch and the skin surface, after the electrode patch is adhesively affixed to the skin.

Figure 6:
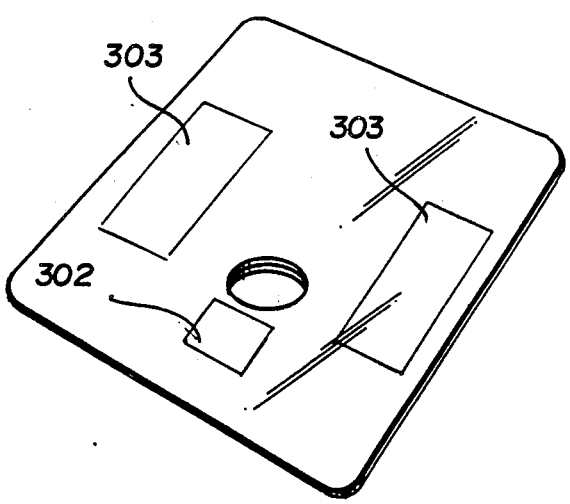
Figure 7:
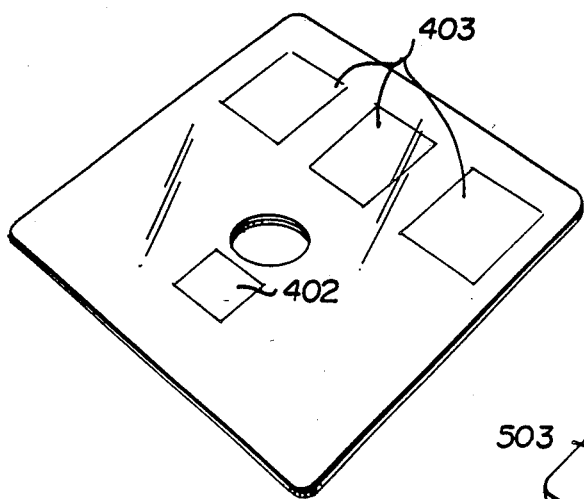
Figure 8:
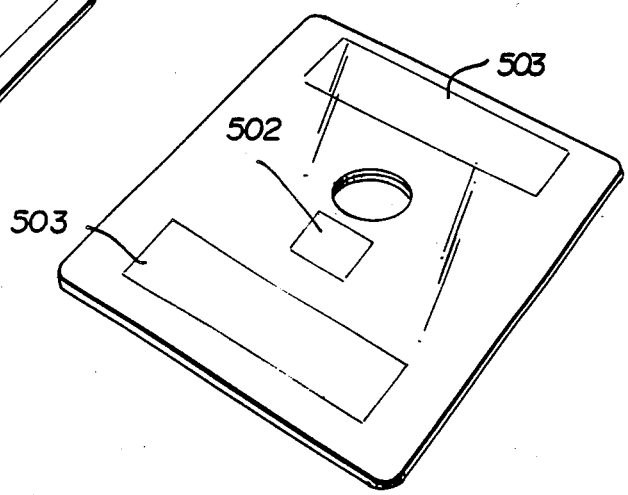
Figure 9:
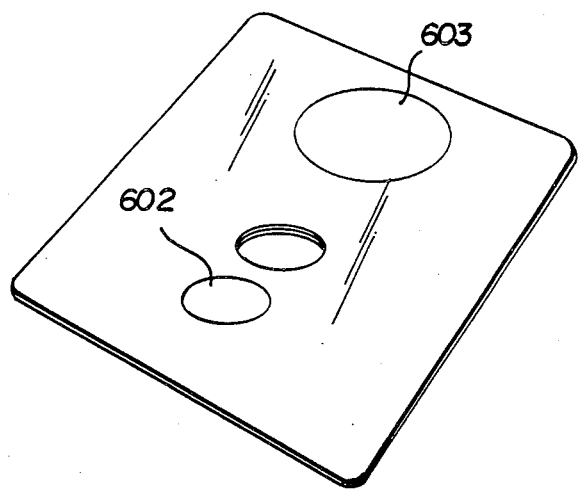

It should be understood that the present invention may incorporate more than two electrodes, that is a treatment electrode and multiple remote electrodes (see FIGS. 6-8). Further, the electrodes may be arranged in a variety of ways and may be of various shapes and sizes. (see FIGS. 6-9). As shown in FIGS. 6-11, electrodes are denoted by numerals 302, 303; 402, 403; 502, 503; 602, 603; 702, 703; and 802, 803. The flexible insulating substrate is generally shown by the out or most boundary lines and is denoted by reference numerals 704 and 804 in FIGS. 10 and 11 respectively.

Figure 11:
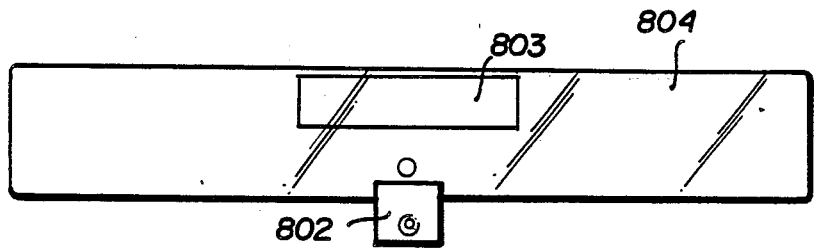

When the electrode structure is to be used on horses, it has been experimentally determined that the border area 130 of adhesive available for affixation should probably be at least about 0.75 inch wide to insure good adhesive affixation. FIG. 11 depicts an alternate embodiment without a continuous adhesive border.

Figure 10:
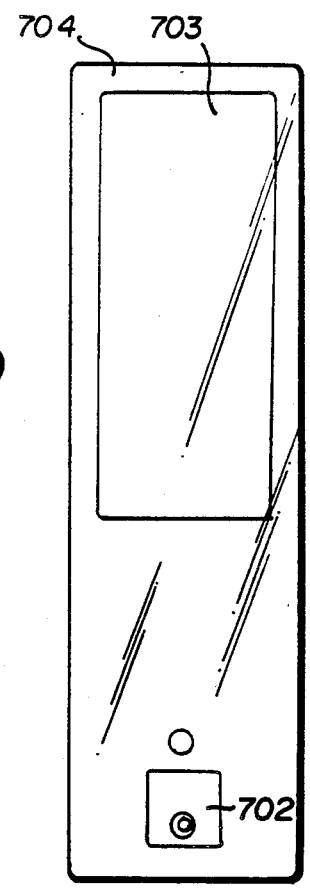
FIGS. 10 and 11 are plan views of two further exemplary embodiments of the electrode structure.

As should be appreciated, other patch shapes may utilize the principles of this invention and, for example, an elongated rectangular patch is depicted in FIG. 10. Similarly, for some applications it may not be necessary or even desirable to have a completely continuous adhesive border about the conductive patches. Accordingly, in such cases, the adhesive-backed flexible insulating patch 104 may have a considerably different size and shape from that of the conductive patches as is, for example, depicted at FIG. 11. It will also be appreciated that the adhesive backing might in some cases be applied directly to the periphery or other desired portions of each conductive electrode structure itself. Each conductive patch may also be formed by printing, painting or otherwise placing conductive ink on a suitable substrate. However, in the present exemplary embodiments, aluminum foil is preferred (e.g., it is conceivable that the ions which make an ink conductive might, over time, migrate under influence of the electrical treatment fields away from the printed ink itself thus deteriorating the overall electrode function).

In the present exemplary embodiment the conductive patch 103 may be approximately 3 inches by 1 inch and the treatment electrode 102 about one inch square, while the insulating patch 104 may be approximately 5×5½ inches in overall dimension. Aperture 116 in the embodiment of FIGS. 1-2 may be approximately 0.688 inch diameter.

It will be understood that the electrode apparatus and method described may also be utilized to achieve conductive coupling to the external skin surfaces of human subjects as well as animals.

Although this invention has been above-described only with respect to a few presently preferred exemplary embodiments, those skilled in the art will recognize that many variations and modifications may be made in these embodiments while yet retaining many of the novel features and advantages of this invention. The following claims are intended to cover all such variations and modifications.

What is claimed is:

1. A multi-element electrode for making electrical contact to the body surface of a living subject, said electrode comprising:
   a first conductive patch having a first area and an electrical connection thereto;
   a second conductive patch having a second area and an electrical connection thereto;
   an adhesive backed-flexible insulating sheet extending at least part way about the edges of said conductive patches which are positioned at predetermined relative locations on said sheet; and
   said adhesive-backed flexible insulating sheet having a treatment location and access aperture extending therethrough at a predetermined asymmetric location relative to said first and second conductive patches.

2. A multi-element electrode as in claim 1 wherein said conductive patches are affixed on one adhesive-coated side of said sheet, and further including a release liner releasably attached to and covering the otherwise remaining exposed adhesive-backing of said sheet prior to its intended usage.

3. A multi-element electrode as in claim 1 wherein said first patch is a treatment cathode electrode and said second patch is an anode electrode wherein said treatment electrode has a smaller surface area than said anode electrode and wherein said treatment electrode is positioned more closely to said treatment aperture.

4. A multi-element electrode as in claim 2 wherein said electrical connections each comprise an electrical snap-on terminal affixed to one of said conductive patches and extending through further apertures in said sheet towards the other side of said sheet.

5. A multi-element electrode as in claim 4 wherein said conductive patches comprise metal foil patches prelaminated with an insulating coating on the side affixed to said sheet and each patch having a doubled-back tab area at which said terminal is affixed with electrical connections being effected to both the exposed top and bottom metal foil surfaces in the double thickness tab area.

6. A multi-element electrode as in claim 1 wherein at least one patch has at least one gel application aperture extending therethrough.

7. A multi-element electrode for therapeutic or diagnostic applications in medical or veterinary use which may be adhesively affixed to the external body surface of a subject, said electrode comprising:
   a plurality of conductive patches for transferring electrical signals to/from the subject;
   an adhesive layer extending at least part way about the edges of said conductive patches which are positioned at predetermined relative locations on said layer for holding said conductive patches at predetermined relative locations and in place on the body surface of a subject;
   at least one treatment location and access aperture being provided in said adhesive layer at a predetermined location relative to said electrodes which defines the proper location of treatment area and which thus facilitates proper placement over an injury or other treatment site and for access to the site; and a releasable liner protectively covering the otherwise exposed adhesive surface of said adhesive layer until the liner is removed to permit affixation to said body surface.

8. A multi-element as in claim 7 wherein each patch has a gel aperture extending therethrough to facilitate surface application of electrode preparation material through each gel aperture.

9. A multi-element as in claim 7 or 8 wherein;
said conductive patches each comprise a metal foil patch;
said adhesive layer comprises an adhesive-backed, flexible insulator patch having an area larger than the combined area of said conductive patches;
said metal foil and insulator patches having aligned apertures therethrough;
said metal foil patches being disposed on and within the adhesively-coated side of said insulator patch at predetermined locations relative to said treatment aperture so that there is a predetermined current density at the injury site when the treatment location and access aperture are disposed in a corresponding predetermined relative location thereat.

10. A multi-element as in claim 9 further comprising a snap-on electrical connector terminal affixed to each of said metal foil patches and extending back through an aperture in said insulator patch for access through the other side thereof.

* * * * *